US008966969B2

(12) United States Patent
Kriel et al.

(10) Patent No.: US 8,966,969 B2
(45) Date of Patent: Mar. 3, 2015

(54) AUTOMATED ANALYSIS OF PRESSURIZED RESERVOIR FLUIDS

(75) Inventors: Wayne A. Kriel, Friendswood, TX (US); Shuzong Cai, The Woodlands, TX (US); Francisco J. Azcarate, Houston, TX (US)

(73) Assignee: SGS North America Inc., Rutherford, NJ (US)

( * ) Notice: Subject to any disclaimer, the term of this patent is extended or adjusted under 35 U.S.C. 154(b) by 673 days.

(21) Appl. No.: 13/184,874

(22) Filed: Jul. 18, 2011

(65) Prior Publication Data
US 2012/0011919 A1  Jan. 19, 2012

Related U.S. Application Data

(60) Provisional application No. 61/365,482, filed on Jul. 19, 2010.

(51) Int. Cl.
*E21B 49/08* (2006.01)
*G01N 30/88* (2006.01)

(52) U.S. Cl.
CPC ........ *G01N 30/88* (2013.01); *G01N 2030/8854* (2013.01)
USPC ...... 73/152.42; 73/64.44; 73/23.38; 73/23.41

(58) Field of Classification Search
CPC .............. G01N 2001/2267; G01N 2001/2229; G01N 2030/025
See application file for complete search history.

(56) References Cited

U.S. PATENT DOCUMENTS

| 3,859,209 | A |   | 1/1975  | Jahnsen       |
|-----------|---|---|---------|---------------|
| 4,409,814 | A |   | 10/1983 | Onuma et al.  |
| 4,773,257 | A |   | 9/1988  | Aslesen et al.|
| 5,235,843 | A |   | 8/1993  | Langhorst     |

(Continued)

FOREIGN PATENT DOCUMENTS

| EP | 0092975 A1 | 11/1983 |
| GB | 2292216 A  * | 2/1996 |

(Continued)

OTHER PUBLICATIONS

Notification of Transmittal of the International Preliminary Report on Patentability (8 pages); mailed Nov. 8, 2012, for related international application PCT/US2011/044396.

(Continued)

*Primary Examiner* — Paul West
(74) *Attorney, Agent, or Firm* — Fish & Richardson P.C.

(57) ABSTRACT

Processing a reservoir fluid sample includes separating the reservoir fluid sample into a vapor phase stream and a liquid phase stream, assessing a composition of the vapor phase stream, sampling a property of the liquid phase steam, and assessing a volume of a components of the liquid phase stream based at least in part on the sampled property of the liquid phase stream. A system for processing a reservoir fluid sample includes a volumetric receptacle adapted to accept the reservoir fluid sample, a phase separator configured to receive the reservoir fluid sample from the volumetric receptacle and to separate the reservoir fluid sample into a vapor phase stream and a liquid phase stream, a gas chromatograph arranged to receive the vapor phase stream from the phase separator, and a liquid flow meter configured to detect an interface including at least one component of the liquid phase stream.

40 Claims, 3 Drawing Sheets

(56) References Cited

U.S. PATENT DOCUMENTS

| | | | |
|---|---|---|---|
| 5,400,657 | A | 3/1995 | Kolpak et al. |
| 5,499,531 | A | 3/1996 | Henderson |
| 5,889,202 | A | 3/1999 | Alapati et al. |
| 6,164,308 | A | 12/2000 | Butler |
| 6,865,926 | B2 | 3/2005 | O'Brien |
| 6,872,571 | B1 * | 3/2005 | Adolfsen et al. ............... 436/53 |
| 6,952,945 | B2 | 10/2005 | O'Brien |
| 7,257,987 | B2 | 8/2007 | O'Brien |
| 7,467,540 | B2 | 12/2008 | Kriel |
| 7,621,171 | B2 | 11/2009 | O'Brien |
| 7,823,656 | B1 * | 11/2010 | Williams ....................... 175/38 |
| 8,347,688 | B2 | 1/2013 | O'Brien |
| 2003/0136185 | A1 | 7/2003 | Dutton et al. |
| 2005/0155906 | A1 | 7/2005 | Wellington et al. |
| 2007/0089483 | A1 | 4/2007 | Kriel |
| 2008/0141767 | A1 | 6/2008 | Raghuraman et al. |
| 2012/0272715 | A1 | 11/2012 | Kriel |

FOREIGN PATENT DOCUMENTS

| | | |
|---|---|---|
| RU | 2229122 C1 | 5/2004 |
| RU | 2404362 C2 | 11/2010 |
| WO | WO2007/041660 | 4/2007 |
| WO | WO2008064402 A1 | 6/2008 |

OTHER PUBLICATIONS

GPA Standard 2286-95, "Tentative Method of Extended Analysis for Natural Gas and Similar Gaseous Mixtures by Temperature Programmed Gas Chromatography," Gas Processors Association, 1999, 22 pages.

GPA Standard 2186-02, "Method for the Extended Analysis of Hydrocarbon Liquid Mixtures Containing Nitrogen and Carbon Dioxide by Temperature Programmed Gas Chromatography," Gas Processors Association, 2002, 22 pages.

GPA Standard 2261-00, "Analysis for Natural Gas and Similar Gaseous Mixtures by Gas Chromatography," Gas Processors Association, 2000, 19 pages.

Burke et al; Extended Analysis of Live Reservoir Oils by Gas Chromatography; SPE International Symposium on Oilfield Chemistry; 1991; pp. 79-86.

International Search Report; WITZIG; Jul. 25, 2012; World Intellectual Property Organization (WIPO) (International Bureau of); PCT/US2012/035445; 15 pages.

W.A. Kriel et al.; "Improved Gas Chromatographic Analysis of Reservoir Gas and Condensate Samples"; Proceedings of the 1993 SPE International Symposium on Oilfield Chemistry; New Orleans, Louisiana, USA; Mar. 2-5, 1993; pp. 397-411.

PCT/US2006/038905 International Search Report and Written Opinion, PCT, Jan. 18, 2007, 14 pages.

PCT/US2006/038905 International Preliminary Report on Patentability, PCT, Jan. 16, 2008, 15 pages.

PCT/US2011/044396 International Search Report and Written Opinion, PCT, Sep. 29, 2011, 11 pages.

Written Opinion of the International Preliminary Examining Authority; Aug. 9, 2012; World Intellectual Property Organization (WIPO) (International Bureau of); PCT/US2011/044396; 6 pages.

Witten Opinion for International Application No. PCT/US2012/035445, dated May 31, 2013, 6 pages.

International Preliminary Report on Patentability for International Application No. PCT/US2012/035445, dated Jul. 9, 2013, 23 pages.

* cited by examiner

AUTOMATED ANALYSIS OF PRESSURIZED RESERVOIR FLUIDS

CROSS-REFERENCE TO RELATED APPLICATION

This application claims priority to U.S. Application Ser. No. 61/365,482 filed on Jul. 19, 2010, which is incorporated by reference herein.

TECHNICAL FIELD

This invention related to automated analysis of reservoir fluids such as live (pressurized) crude oil.

BACKGROUND

Reservoir fluids typically exist or are produced at elevated pressures and temperatures, and include a mixture of hydrocarbon gases (e.g., natural gas) and complex hydrocarbon fluids generally referred to as "oil" or "condensate." There are instances where it is desired to determine properties of a reservoir fluid for reservoir management purposes, such as to determine gas to oil ratios (GOR), fluid shrinkage, American Petroleum Institute (API) gravity, and hydrocarbon composition. These data are utilized widely in reserve estimations, reservoir simulation, pressure transient testing, production allocations, and the like. Although some offshore platforms maintain a small laboratory for determination of basic fluid properties, space on the platform may not permit the equipment necessary to analyze the fluid in detail. In some cases, it is not practical to maintain the voluminous analysis equipment at remote sampling sites, such as deep water offshore platforms, remote locations, underdeveloped countries, and rural areas. Therefore, a sample taken on an offshore platform may be transported to an onshore testing facility. Depending on the location of the offshore platform or rural onshore sampling site, the sample may travel hundreds or thousands of miles to reach the testing facility. Due at least in part to transportation regulations on pressurized petroleum fluids, this travel can introduce a considerable lag between the time the sample is taken and the time the analysis is performed. This time lag can be excessive and in some cases impractical, discouraging frequent testing and reducing or eliminating retesting. The travel increases the likelihood that the sample will become compromised and/or contaminated, and introduces additional expenses related to travel and time into the costs of analysis. If a sample is contaminated or fouled during collection, transport, or otherwise, the contamination or fouling may not be discovered until the sample has traveled the many miles to reach the centralized testing facility. In such cases, when possible, another sample is then taken and transported to the centralized testing facility.

In some cases, the headspace vapor from a liquid, rather than the liquid itself, may be analyzed in a laboratory on an offshore platform. While this approach allows analysis at the site, more information regarding the liquid may be desired. Furthermore, when analysis of reservoir fluids includes flash vaporization, a separate apparatus may be required to flash the sample and collect the liquid and vapor phases, in which case the liquid and vapor phases are typically transferred to another apparatus for compositional analysis. These operations are generally implemented by skilled personnel stationed at the offshore platform.

SUMMARY

Implementations of the present disclosure are directed to devices, systems, and techniques for automated analysis of a reservoir fluid sample, such as a pressurized reservoir fluid sample (e.g., live crude).

In a first general aspect, processing a reservoir fluid sample includes separating the reservoir fluid sample into a vapor phase stream and a liquid phase stream, assessing a composition of the vapor phase stream with a first gas chromatograph, sampling a property of the liquid phase stream, and assessing a volume of a component of the liquid phase stream based at least in part on the sampled property of the liquid phase stream or on a change in the sampled property of the liquid phase stream. Sampling the property may be automated. That is, sampling the property may occur without human observation or interaction.

In a second general aspect, a system for processing a reservoir fluid sample includes a volumetric receptacle adapted to accept the reservoir fluid sample, a phase separator configured to receive the reservoir fluid sample from the volumetric receptacle and to separate the reservoir fluid sample into a vapor phase stream and a liquid phase stream, a gas chromatograph arranged to receive the vapor phase stream from the phase separator, and a liquid flow meter configured to detect an interface including at least one component of the liquid phase stream.

These and other implementations may each optionally include one or more of the following features. For example, processing a reservoir fluid sample may include assessing a volume of the reservoir fluid sample before separating the reservoir fluid sample into the vapor phase stream and the liquid phase stream. In some cases, assessing the volume of the reservoir fluid sample includes providing the reservoir fluid sample from a pressurized fluid source to a volumetric receptacle. Processing a reservoir fluid sample may include assessing a temperature and a pressure of the vapor phase stream, assessing a volume of the vapor phase stream, assessing an energy content of the vapor phase stream, or a combination thereof.

In some cases, assessing a volume of a component of the liquid phase stream based at least in part on the sampled property of the liquid phase stream includes sampling a temperature of the liquid phase stream, sampling a temperature gradient of a portion of the liquid phase stream, or sampling a transmittance of the liquid phase stream. Assessing a volume of a component of the liquid phase stream based at least in part on the sampled property of the liquid phase stream may include assessing a volume of an aqueous component in the liquid phase stream, assessing a volume of an oil component in the liquid phase stream, or both. In certain cases, assessing a volume of a component of the liquid phase stream based at least in part on the sampled property of the liquid phase stream includes flowing the liquid phase stream through a liquid flow meter.

Processing a reservoir fluid sample may include assessing a density of at least a portion of the liquid phase stream. Assessing the density of at least the portion of the liquid phase stream can include, for example, flowing the liquid phase stream through a density meter. In some embodiments, processing a reservoir fluid sample includes assessing a gas to oil ratio of fluid shrinkage, or API gravity of the reservoir fluid sample, or a combination thereof. In some cases, processing a reservoir fluid sample includes assessing a composition of at least a portion of the liquid phase stream with a second gas chromatograph.

A system for processing a reservoir fluid sample may include a gas meter configured to assess a volume of the vapor phase stream, a pressure sensor configured to assess a pressure of the vapor phase stream, a temperature sensor configured to assess a temperature of the vapor phase stream, or a combination thereof. In some cases, a system for processing a reservoir fluid sample includes a pump configured to pump the liquid phase stream from the phase separator through the liquid flow meter.

In some cases, a system for processing a reservoir fluid sample includes a second volumetric receptacle adapted to receive the liquid phase stream, a density meter configured to assess a density of at least a portion of the liquid phase stream, a second gas chromatograph arranged to receive at least a portion of the liquid phase stream, or any combination thereof. In certain cases, system for processing a reservoir fluid sample includes a controller (e.g., a computing device such as a laptop or desk top computer). The controller may be coupled to a network and one or more remote computing devices. The controller can be configured to control a flow of the reservoir fluid, the gas phase stream, the liquid phase stream, or a combination thereof. For example, the controller may be configured to initiate flow of the reservoir fluid sample to the volumetric receptacle (e.g., at a pre-selected time, interval, or combination thereof). In some cases, the controller is configured to control a flow rate of the reservoir fluid from the volumetric receptacle to the phase separator. In certain cases, the controller is configured to initiate flow of the liquid phase stream from the phase separator in response to removal of substantially all of the gas phase stream from the phase separator. The controller may be configured to select a source of the reservoir fluid sample (e.g., from a multiplicity of high pressure fluid sources).

These general and specific aspects may be implemented using a device, system or method, or any combination of devices, systems, or methods. The details of one or more embodiments are set forth in the accompanying drawings and the description below. Other features, objects, and advantages will be apparent from the description and drawings, and from the claims.

BRIEF DESCRIPTION OF THE DRAWINGS

The concepts herein may be more completely understood in consideration of the following detailed description of various embodiments in connection with the accompanying drawings, in which.

DETAILED DESCRIPTION

Figure 1:
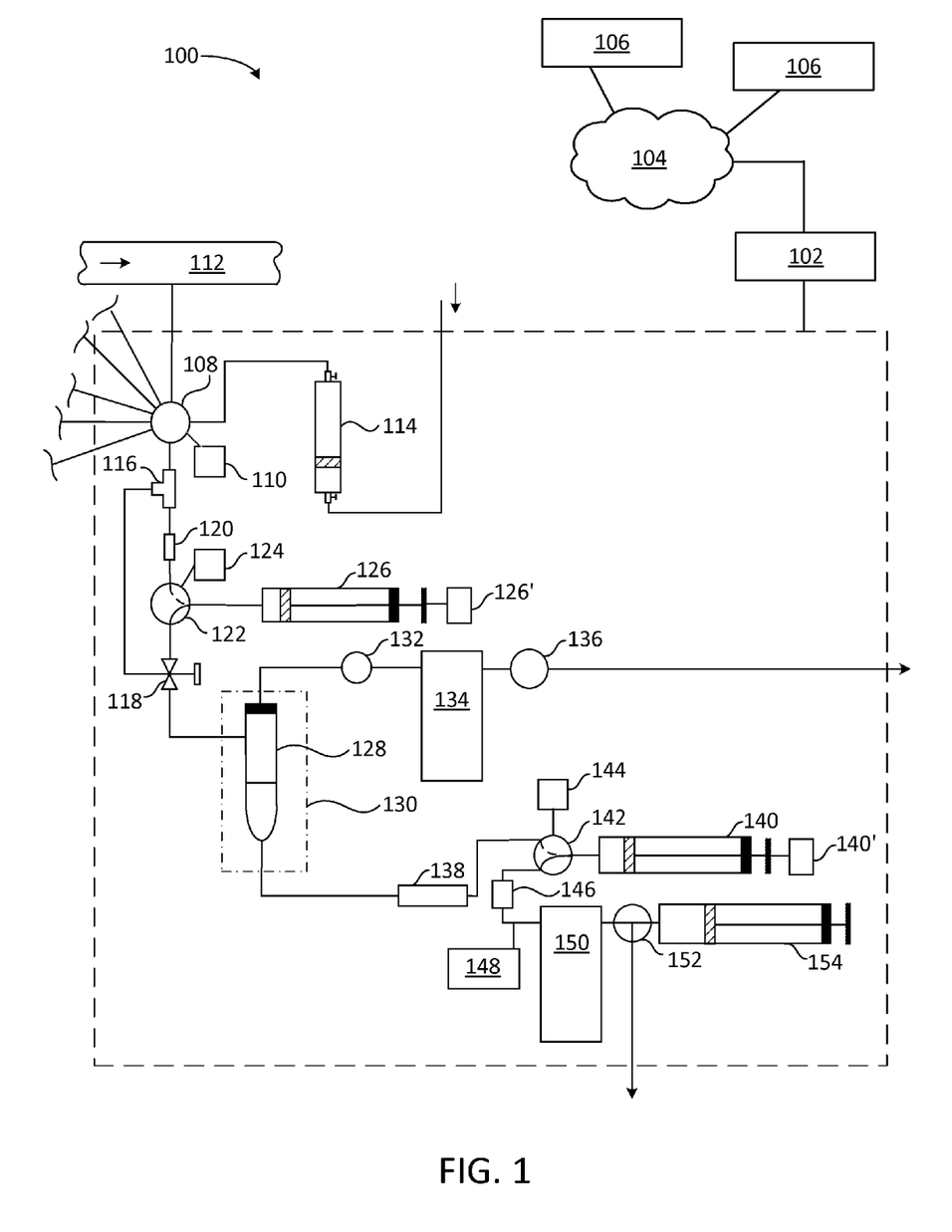
FIG. 1 depicts an illustrative system for processing a reservoir fluid sample.

Referring to FIG. 1, system 100 for processing a reservoir fluid sample is a portable system capable of continuous, unattended gas to oil ratio (GOR) measurements and other measurements typically performed in a fixed laboratory. System 100 can be deployed to offshore or remote locations, thereby eliminating difficulties associated with transporting pressurized reservoir fluid. System 100 allows properties of a reservoir fluid sample to be assessed rapidly at relatively low cost, with high accuracy and precision. In some cases, system 100 can be enclosed in a climate-controlled housing suitable for hazardous environments, such as a National Electrical Manufacturers Association (NEMA) Class 1, Division 2 housing. System 100 includes controller 102 coupled to components of the system such that processing a reservoir fluid sample can be partially automated (e.g., automatically assessing a sample provided by a user) or completely automated (e.g., automatically sampling and assessing a pressurized reservoir fluid). Controller 102 may be, for example, a laptop or desk top computer or other computing device. Controller 102 may incorporate dedicated software or generic software, e.g. a spreadsheet, that facilitates performing the calculations and/or recording and storing data. In certain cases, controller 102 is linked to network 104 that allows remote computing devices 106 to communicate with controller 102.

As described herein, system 100 is capable of assessing a volume of a pressurized reservoir fluid sample at a known temperature and pressure, as well as a volume of a vapor phase stream and a liquid phase stream evolved from the pressurized reservoir fluid sample. System 100 is also capable of automatically assessing a temperature and pressure of gas in the vapor phase stream, gas to oil ratio and fluid shrinkage of the pressurized reservoir fluid sample, and API gravity of at least a portion of the liquid phase. Composition of the liberated vapor phase and liquid phase can also be assessed, along with other properties useful in reserve estimation, reservoir simulation, pressure transient testing, well completion, and production allocation, and the like.

Valve 108 is coupled to valve controller 110 and to one or more (e.g., two to twenty) high pressure fluid sources. In an example, valve 108 is a 12-way, high pressure valve (e.g., model EMTCSD12UW available from Valco Instruments Co. Inc., Houston, Tex.) coupled to up to 12 different sources of pressurized reservoir fluid. Sources of pressurized reservoir fluid may include, for example, any combination of conduits 112 transporting live crude (e.g., pipelines or wellheads) and sample vessels 114 with live crude samples. Valve controller 110 is coupled to controller 102 such that the source of the reservoir fluid sample to be processed by system 100 can be selected remotely as needed or based on a pre-selected sampling program.

Figure 2:
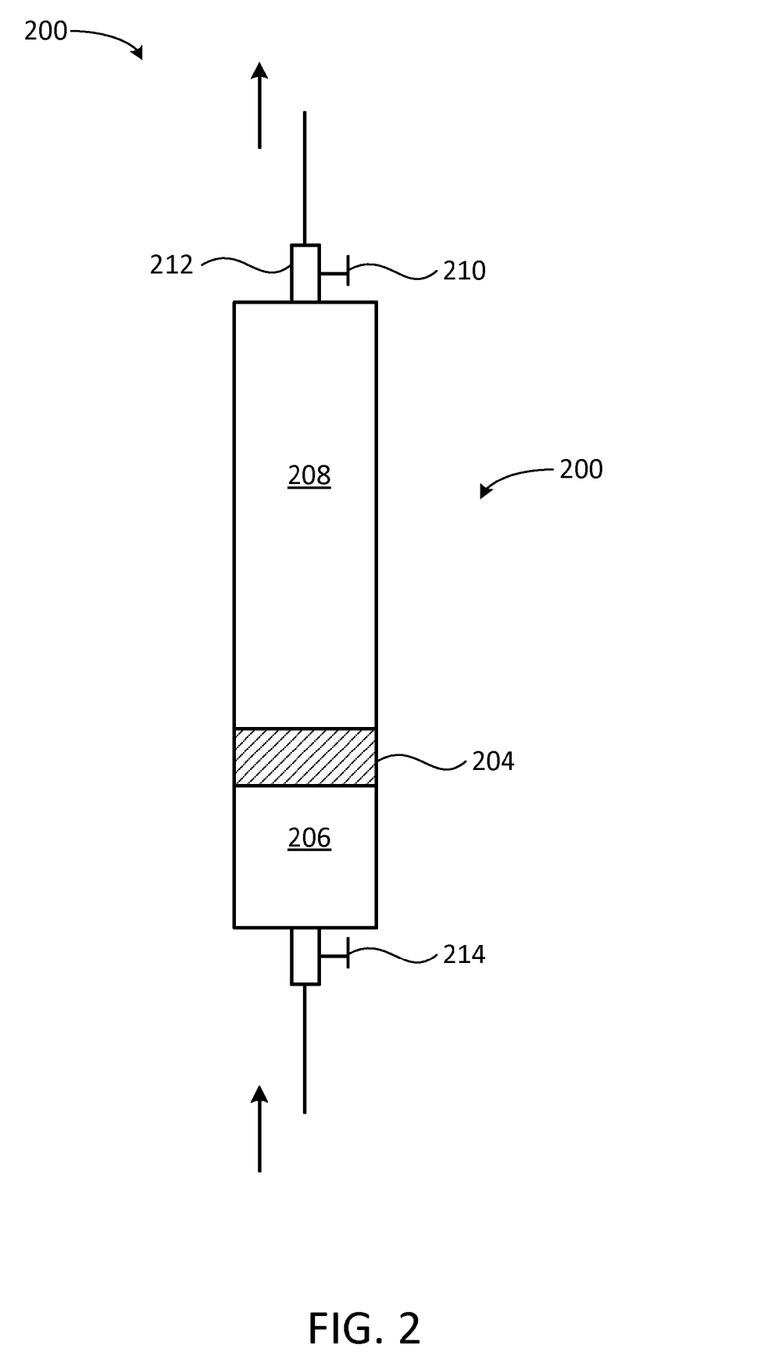
FIG. 2 depicts an illustrative sample vessel for providing a pressurized reservoir fluid sample to a system for processing a reservoir fluid sample.

One example of a sample vessel is described in U.S. Pat. No. 7,467,540, which is incorporated by reference herein. As shown in FIG. 2, sample vessel 200 internally defines elongate cavity 202 that sealingly receives piston 204. Piston 204 divides elongate cavity 202 into two distinct chambers: a drive fluid chamber 206 and a sample chamber 208. Sample chamber 208 is operable to receive a fluid sample through sample valve 210. After receiving the fluid sample, sample valve 210 may be closed to retain the fluid sample in sample chamber 208.

In certain embodiments, sample vessel 200 may be configured to operate as a pycnometer. To this end, the maximum volume of sample vessel 200 is calibrated for a known pressure and temperature. Additionally, the "dry" weight of sample vessel 200 is known. The volume of the fluid sample, thus, may be determined by adjusting the maximum volume of sample chamber 208 for the temperature and pressure of the fluid sample therein. The weight of the fluid sample may be determined by weighing sample vessel 200 containing the fluid sample, and subtracting the dry weight of the sample vessel. The density of the fluid sample may be determined by dividing the determined volume by the determined weight.

In certain embodiments, a size of sample vessel 200 may be selected to facilitate handling by the operator. In one instance, sample vessel 200 has an internal volume of 10 cc when calibrated at 10 MPa and 20° C. and is constructed from 316 stainless steel. To facilitate removal and return of sample vessel 200 to system 100, an outlet of the sample vessel may be coupled to a quick release connection 212 that allows easy installation and removal of sample vessel 200 from valve 108. In certain embodiments, low dead volume fittings are used in one or more locations of system 100, for example, the connections with valve 108.

As noted above, sample vessel 200 includes piston 204 that divides elongate cavity 202 into two distinct chambers: drive fluid chamber 206 and sample chamber 208. Sample vessel 200 may further include drive valve 214 provided in communication with drive fluid chamber 206. With drive valve 214 open, receiving the fluid sample in sample chamber 208 drives piston 204 in elongate cavity 202 to expand sample chamber 208 and reduce a volume of drive fluid chamber 206. A drive fluid (e.g., a pressurized gas such as $CO_2$ or a pressurized liquid such as water) may be introduced through drive valve 214 to pressurize drive fluid chamber 206 and drive the fluid sample from sample chamber 208 toward valve 108. In some cases, the fluid sample may be evacuated from sample chamber 208 in other manners. For example, a mechanical or electromechanical system, such as a motor and a gear train or screw drive, may be used to move piston 204.

In the illustrative example shown in FIG. 2, drive fluid in drive fluid chamber 206 exerts pressure, via piston 204, on the fluid sample in sample chamber 208. When sample valve 210 is opened, the pressure in sample chamber 208 drops. Pressure in drive fluid chamber 206 drives piston 204 to reduce a volume of sample chamber 208 and thus drive the fluid sample out of sample vessel 200. In some instances, for example where the fluid sample is live crude under pressure, the fluid sample may become two phase (i.e. vapor and liquid) when sample valve 210 is opened and pressure within sample chamber 208 drops. The heavier liquid phase of the fluid sample then accumulates about the bottom of sample chamber 208, and the vapor phase of the fluid sample accumulates at the top of the sample chamber. Movement of piston 204 expels the vapor phase and the liquid phase of the fluid sample through valve 108.

Referring again to FIG. 1, once a high pressure fluid source has been selected at valve 108, the reservoir fluid sample flows from the source to splitter 116. A portion of the sample flows from splitter 116 to low dead volume back pressure regulator 118 (e.g., model EB1HP1-SS316 available from Equilibar, LLC, Fletcher, N.C.). Another portion of the sample flows from splitter 116 to filter 120 to remove particulates from the reservoir fluid sample. In an example, filter 120 is a 0.5 μm filter (e.g., model 15-51AF2 available from High Pressure Equipment Company, Erie, Pa.). From filter 120, the reservoir fluid sample flows to valve 122. Valve 122 is controlled by valve controller 124 coupled to controller 102, and may be, for example, a 3-way valve (e.g., model DC3UW/EMT available from Valco Instruments Co. Inc., Houston, Tex.). With valve 122 in the "load" position, volumetric receptacle 126 is filled with the reservoir fluid sample. In some embodiments, a volume of volumetric receptacle 126 is in a range between 2 cc and 20 cc. In an example, a volume of volumetric receptacle 126 is 8 cc. In some embodiments, volumetric receptacle 126 includes or is coupled to pump 126'. In certain embodiments, volumetric receptacle 126 is a high pressure, high precision syringe pump (available, e.g., from cetoni GMBH, Germany) coupled to controller 102.

With volumetric receptacle 126 filled with the reservoir fluid sample, a volume of the sample is assessed. With valve 122 in the "deliver" position, the reservoir fluid sample flows through the valve and toward back pressure regulator 118, where back pressure is provided by a portion of the reservoir fluid sample from splitter 116. Fluid from volumetric receptacle 126 is provided to phase separator 128 at a controlled rate (e.g., in a range between about 0.1 cc/min and about 10 cc/min, or about 1 cc/min) through back pressure regulator 118. Back pressure regulator 118 may serve as a restriction or metering valve, causing the reservoir fluid sample released from the back pressure regulator to undergo a single stage flash, allowing the reservoir fluid sample to separate into a vapor phase, typically including natural gas, and a liquid phase, typically including an oil component and an aqueous component. The oil component generally includes naturally occurring hydrocarbons present in crude oils and condensates. The flash is generally maintained under constant pressure and temperature in enclosure 130 (e.g., by suitable heating and cooling apparatus, together with a temperature controller coupled to controller 102), until substantially all of the liquid in volumetric receptacle 126 is depleted.

The vapor phase stream is allowed to exit from phase separator 128. Temperature and pressure of the vapor phase stream are assessed by pressure/temperature sensor 132 coupled to controller 102. The vapor phase stream then enters gas chromatograph 134 through a gas sampling valve, and a composition of the vapor phase is assessed in accordance with GPA 2286 ("Tentative Method of Extended Analysis for Natural Gas and Similar Gaseous Mixtures by Temperature Programmed Gas Chromatography," Revised 1995, Gas Processors Association), which is incorporated herein by reference. An energy content of the vapor phase stream may be assessed based at least in part on data from gas chromatograph 134. The vapor phase stream exiting from gas chromatograph 134 flows through gas meter 136 (available, e.g., from Agilent Technologies, Santa Clara, Calif.) coupled to controller 102, and a volume of the vapor phase stream is assessed. The vapor phase stream exiting from the gas meter 136 is vented to atmosphere or further processed as needed.

In response to the cessation of vapor evolution and/or decreased gas flow through gas meter 136 indicative of substantial completion of the flash, controller 102 initiates flow of the liquid phase stream from phase separator 128. In an example, controller 102 initiates flow of the liquid phase stream from phase separator 128 by engaging a pump to draw the fluid from the phase separator through liquid flow meter 138. In an example, controller 102 initiates volumetric receptacle 140, which may include or be coupled to pump 140', to withdraw liquid from phase separator 128 through valve 142 coupled to valve controller 144. Valve 142 may be a 3-way valve (e.g., model DC3UW/EMT available from Valco Instruments Co. Inc., Houston, Tex.). Volumetric receptacle 140 may be a mid pressure, high precision syringe pump (available, e.g., from cetoni GMBH, Germany).

As liquid is withdrawn from phase separator 128, the liquid phase stream flows through liquid flow meter 138. Liquid flow meter 138, coupled to controller 102, monitors or samples one or more properties of the liquid phase stream. A property monitored or sampled may be, for example, a temperature of the liquid phase stream, a temperature gradient across a portion of the liquid phase stream, light transmittance (e.g., visible or ultraviolet transmittance) of the liquid phase stream. The property of the liquid phase stream may be monitored or sampled automatically at a pre-selected time interval, and a volume of one or more components of the liquid phase stream, the flow of which can be plug flow in nature, can be assessed based at least in part on the sampled property of the liquid phase stream. The sampled property may also be used to detect an interface between components in the liquid phase stream (e.g., an oil component and an aqueous component) or an interface including a component in the liquid phase stream (e.g., an oil component) and gas from the phase separator following the liquid phase stream. When the presence of gas following the liquid phase stream (or an interface between a component of the liquid phase stream and the gas) is detected by liquid flow meter 138, the liquid components are understood to be substantially completely removed from phase separator 128. Suitable liquid flow meters include, for example, model ASL-1600-20 available from Sensirion AG, Switzerland and LIQUI-FLOW Series L10/L20 Digital Mass Flow Meters/Controllers available from BRONKHORST, The Netherlands.

In an example, liquid flow meter 138 assesses a temperature gradient of a portion of the liquid phase stream as the liquid phase stream flows through a capillary with a heating element. The temperature gradient is based at least in part on the thermal conductivity and the flow rate of the fluid in the capillary. The liquid flow meter is configured to provide a flow rate of the liquid phase stream based at least in part on the assessed temperature or temperature gradient. Since the thermal conductivity of components (e.g., the oil component and the aqueous component) in the liquid phase stream differs, a volume of a component (or components) of the liquid phase stream can be assessed based at least in part on the sampled property (e.g., the temperature or temperature gradient) of the liquid phase stream. Additionally, data from liquid flow meter 138 can be used to detect an interface between components of the liquid phase stream or including at least one component of the liquid phase stream (e.g., an interface between one component of the liquid phase stream, such as the oil component and a gas). The identification of at least one interface including at least one component of the liquid phase stream, volumetric data from volumetric receptacle 140, and, optionally flow rate data from liquid flow meter 138, allow assessment of the volume of at least one of the components (e.g., the oil component, the aqueous component, or both) in the liquid phase stream.

Once substantially all of the liquid phase stream is in volumetric receptacle 140, and the volume of one or more components of the liquid phase stream has been assessed, valve 142 is set to "deliver," and the liquid phase stream is allowed to flow (e.g., is pumped) through valve 142 and through density meter 146, which assesses a density of at least a portion (e.g., at least the oil component) of the liquid phase stream. Suitable density meters include L-Dens 313 Stainless steel 316Ti Online Density Transmitter (available, e.g., from Anton Paar GmbH, Austria). In some embodiments, pump or injector 148 is positioned between density meter 146 and gas chromatograph 150. Pump or injector 148, coupled to controller 102, provides a suitable amount of the liquid phase stream to a liquid sampling valve coupled to gas chromatograph 150.

A composition of at least a portion of the liquid phase stream (e.g., a composition of the oil component) is assessed by gas chromatograph 150 in accordance with a modified version (i.e. External Standard Quantification and grouping by pseudocomponents) of GPA Standard 2186-02 ("Method for the Extended Analysis of Hydrocarbon Liquid Mixtures Containing Nitrogen and Carbon Dioxide by Temperature Programmed Gas Chromatography," Revised and Adopted as a Standard 2002, Gas Processors Association), which is incorporated by reference herein. Components of the sample, including C1-C35 and the non-elution portion (C36+) total 100 wt %, with hydrocarbons eluting after n-pentane grouped and quantified as pseudo components, with the exception of a number of cyclic and aromatic compounds.

The liquid flowing from gas chromatograph 150 may flow through selector valve 152. Selector valve 152 may be coupled to valve controller 156. Controller 102, coupled to valve controller 156, may select a position of selector valve 152, thereby directing flow of the liquid phase stream to exit system 100 or to liquid accumulator 154. Liquid accumulator 154 may accumulate liquid from one or more reservoir fluid samples. In some cases, liquid accumulator 154 may be uncoupled from system 100 and transported to a fixed laboratory for additional analysis of liquid in the liquid accumulator.

Gas chromatographs 134 and 150 can communicate with controller 102 to enable local or remote viewing, analysis, and manipulation of the data output from the gas chromatographs and/or other components of system 100. The composition of the oil component of the liquid phase stream from gas chromatograph 150 may be combined with the compositional analysis of the vapor phase stream from gas chromatograph 134 using standard practices to produce a "live fluid" composition. In an example, the live fluid composition can be used for computer model simulations to determine fluid phase behavior and thus fluid ownership or allocation. One or more of the calculations described above can be performed by controller 102.

As described herein, in addition to composition of the reservoir fluid sample, system 100 can provide the volume of the vapor phase stream (or liberated gas) as assessed by gas meter 136 and the volume of at least a portion of the liquid phase stream (e.g., the liberated oil component or aqueous component) as assessed by the coupling of volumetric receptacle 140 and liquid flow meter 138. System 100 can also provide the gas to oil ratio (GOR) of the reservoir fluid sample based on the ratio of the volume of the vapor phase stream to the volume of oil in the liquid phase stream corrected to standard temperature and pressure, as well as API gravity and the fluid shrinkage based on the ratio of the volume of oil in the liquid phase stream and the initial volume of the reservoir fluid sample, as assessed by volumetric receptacle 126.

After analysis of a reservoir fluid sample from a first high pressure fluid source coupled to valve 108, components of system 100 may be purged in preparation for analysis of a subsequent sample. A second high pressure fluid source may be selected, or a second sample from the first high pressure fluid source may be selected.

Although described with particular components arranged in a particular order, components in system 100 may be arranged in configuration different from that illustrated in FIG. 1. Additionally, one or more of the components may be omitted, or additional components may be added. For example, pump/injector 148 may be omitted or an additional gas chromatograph may be added.

Figure 3:
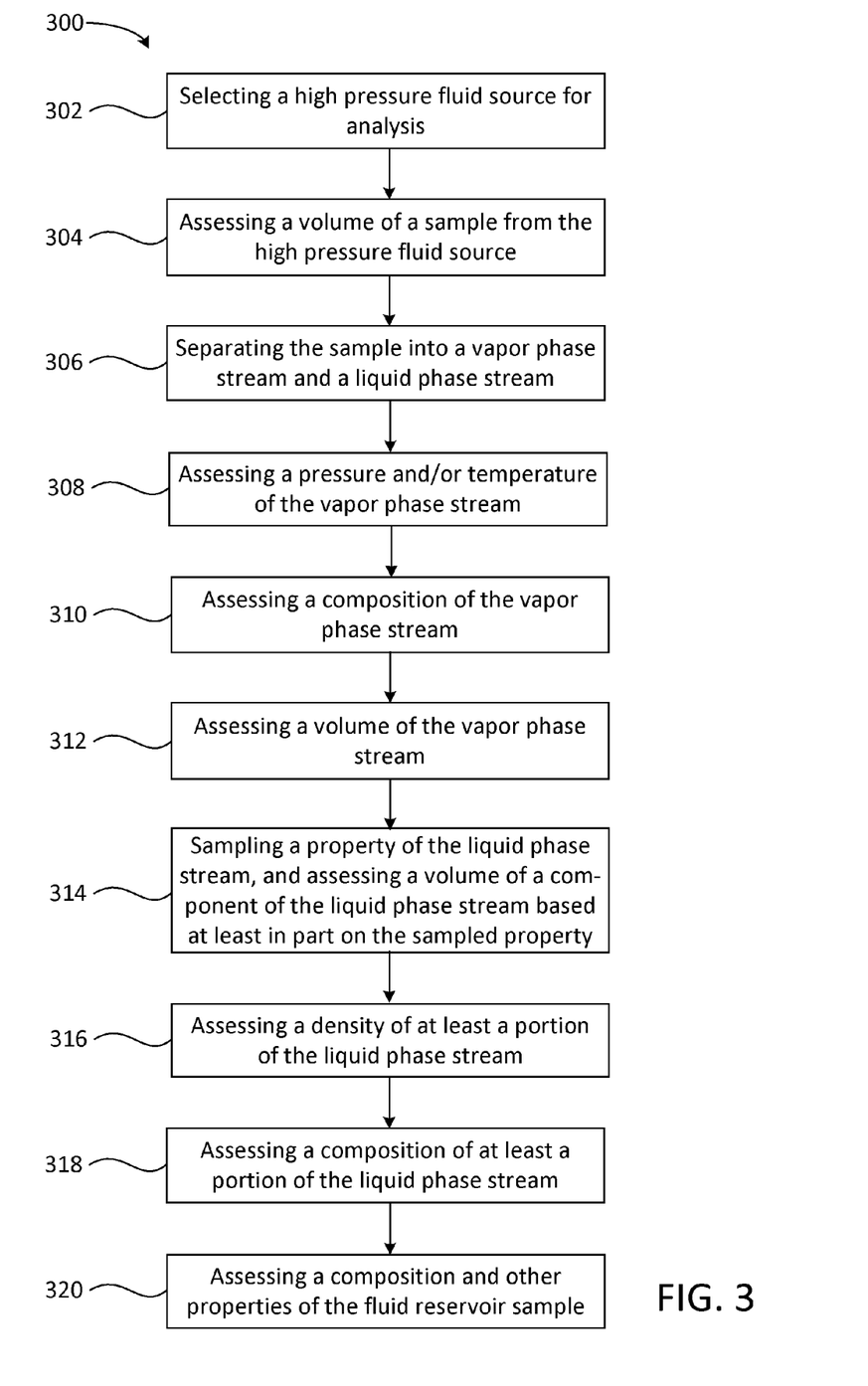
FIG. 3 is a flow diagram of an illustrative method of processing a reservoir fluid sample.

An illustrative method 300 of analyzing a high pressure reservoir fluid enabled by the illustrative system 100 is described with reference to FIG. 3. In the illustrative method, a high pressure fluid source is selected in operation 302. In operation 304, the volume of a reservoir fluid sample from the high pressure fluid source is assessed. The reservoir fluid sample is separated into a vapor phase stream and a liquid phase stream in operation 306. Separating the reservoir fluid sample can be achieved, for example, by flashing the reservoir fluid sample at a controlled temperature and pressure. In operation 308, pressure and temperature of the vapor phase stream is assessed. In operation 310, a composition of the vapor phase stream is assessed (e.g., by a first gas chromatograph). In some cases, an energy content of the vapor phase stream may be assessed based at least in part on the composition of the vapor phase stream. In operation 312, a volume of the vapor phase stream is assessed (e.g., by a flow through gas meter). The vapor phase stream can be vented to the atmosphere.

After substantially all of the reservoir fluid sample has been flashed, as indicated by a decreased flow of gas through the gas meter, analysis of the liquid phase stream is initiated. In an example, a controller responsive to a decreased flow of gas through the gas meter initiates flow of the liquid phase sample from a phase separator, thereby initiating analysis of the liquid phase stream. Operation 314 includes sampling a property of the liquid phase stream, and assessing a volume of a component of the liquid phase stream based at least in part on the sampled property of the liquid phase stream. Operation 314 may also include monitoring a volume of the liquid phase stream (e.g., with a volumetric receptacle such as a syringe pump coupled to a controller).

In operation 316, a density of at least a portion of the liquid phase stream (e.g., the oil component) is assessed (e.g., with a density meter). In operation 318, a composition of the liquid phase stream is assessed (e.g., with a second gas chromatograph). The liquid phase stream exiting from the gas chromatograph can be drained or collected in a fluid accumulator for additional analysis (e.g., at another location).

In operation 320, a composition of the reservoir fluid sample can be assessed by combining data provided to a controller by the first gas chromatograph and the second gas chromatograph. Gas to oil ratio, fluid shrinkage, API gravity, and other useful relationships can be assessed in operation 320 based on data collected by system 100 as described by method 300.

Although described in a particular order, the operations described above may be performed in a different order. Additionally, one or more of the steps may be omitted, or additional steps may be added.

A number of embodiments of the invention have been described. Nevertheless, it will be understood that various modifications may be made without departing from the spirit and scope of the invention. Accordingly, other embodiments are within the scope of the following claims. Further modifications and alternative embodiments of various aspects will be apparent to those skilled in the art in view of this description. Accordingly, this description is to be construed as illustrative only. It is to be understood that the forms shown and described herein are to be taken as examples of embodiments. Elements and materials may be substituted for those illustrated and described herein, parts and processes may be reversed, and certain features may be utilized independently, all as would be apparent to one skilled in the art after having the benefit of this description. Changes may be made in the elements described herein without departing from the spirit and scope as described in the following claims.

What is claimed is:

1. A method of processing a reservoir fluid sample, the method comprising:
    separating the reservoir fluid sample into a vapor phase stream and a liquid phase stream;
    assessing a composition of the vapor phase stream with a first gas chromatograph;
    flowing the liquid phase stream through a liquid flow meter in response to removal of substantially all of the vapor phase stream from the reservoir fluid sample;
    sampling a property of the liquid phase stream flowing through the liquid flow meter; and
    assessing a volume of an oil component or an aqueous component of the liquid phase stream based at least in part on the sampled property of the liquid phase stream,
    wherein assessing the volume of the oil component or the aqueous component of the liquid phase stream comprises detecting an interface comprising at least one component of the liquid phase stream.

2. The method of claim 1, further comprising assessing a volume of the reservoir fluid sample before separating the reservoir fluid sample into the vapor phase stream and the liquid phase stream.

3. The method of claim 2, wherein assessing the volume of the reservoir fluid sample comprises providing the reservoir fluid sample from a pressurized fluid source to a volumetric receptacle.

4. The method of claim 1, further comprising assessing a temperature and a pressure of the vapor phase stream.

5. The method of claim 1, further comprising assessing a volume of the vapor phase stream.

6. The method of claim 1, further comprising assessing an energy content of the vapor phase stream.

7. The method of claim 1, wherein assessing the volume of the component of the liquid phase stream based at least in part on the sampled property of the liquid phase stream comprises sampling a temperature of the liquid phase stream.

8. The method of claim 1, further comprising assessing a density of at least a portion of the liquid phase stream.

9. The method of claim 8, wherein assessing the density of at least the portion of the liquid phase stream comprises flowing the liquid phase stream through a density meter.

10. The method of claim 1, further comprising assessing a gas to oil ratio of the reservoir fluid sample.

11. The method of claim 1, further comprising assessing fluid shrinkage of the reservoir fluid sample.

12. The method of claim 1, further comprising assessing a composition of at least a portion of the liquid phase stream with a second gas chromatograph.

13. A system for processing a reservoir fluid sample, the system comprising:
    a volumetric receptacle adapted to accept the reservoir fluid sample;
    a phase separator configured to receive the reservoir fluid sample from the volumetric receptacle and to separate the reservoir fluid sample into a vapor phase stream and a liquid phase stream;
    a gas chromatograph arranged to receive the vapor phase stream from the phase separator;
    a liquid flow meter configured to detect an interface between an oil component and an aqueous component of the liquid phase stream; and
    a controller,
    wherein the controller is configured to initiate flow of the liquid phase stream from the phase separator in response to removal of substantially all of the vapor phase stream from the phase separator.

14. The system of claim 13, further comprising a gas meter configured to assess a volume of the vapor phase stream.

15. The system of claim 13, further comprising a pressure sensor configured to assess a pressure of the vapor phase stream.

16. The system of claim 13, further comprising a temperature sensor configured to assess a temperature of the vapor phase stream.

17. The system of claim 13, further comprising a pump configured to pump the liquid phase stream from the phase separator through the liquid flow meter.

18. The system of claim 13, further comprising a second volumetric receptacle adapted to receive the liquid phase stream.

19. The system of claim 13, further comprising a density meter configured to assess a density of at least a portion of the liquid phase stream.

20. The system of claim 13, further comprising a second gas chromatograph arranged to receive at least a portion of the liquid phase stream.

21. The system of claim 13, wherein the controller is configured to control a flow of the reservoir fluid, the vapor phase stream, the liquid phase stream, or a combination thereof.

22. The system of claim 13, wherein the controller is configured to initiate flow of the reservoir fluid sample to the volumetric receptacle.

23. The system of claim 13, wherein the controller is configured to initiate flow of the reservoir fluid sample to the volumetric receptacle at a pre-selected time, interval, or combination thereof.

24. The system of claim 13, wherein the controller is configured to control a flow rate of the reservoir fluid from the volumetric receptacle to the phase separator.

25. The system of claim 13, wherein the controller is configured to select a source of the reservoir fluid sample.

26. The system of claim 13, wherein the liquid flow meter is configured to detect an interface between the oil component of the liquid phase stream and a gas.

27. A system for processing a reservoir fluid sample, the system comprising:
a volumetric receptacle adapted to accept the reservoir fluid sample;
a phase separator configured to receive the reservoir fluid sample from the volumetric receptacle and to separate the reservoir fluid sample into a vapor phase stream and a liquid phase stream;
a gas chromatograph arranged to receive the vapor phase stream from the phase separator;
a liquid flow meter configured to detect an interface comprising at least one component of the liquid phase stream; and
a controller,
wherein the controller is configured to initiate flow of the liquid phase stream from the phase separator in response to removal of substantially all of the vapor phase stream from the phase separator.

28. The system of claim 27, further comprising a gas meter configured to assess a volume of the vapor phase stream.

29. The system of claim 27, further comprising a pressure sensor configured to assess a pressure of the vapor phase stream.

30. The system of claim 27, further comprising a temperature sensor configured to assess a temperature of the vapor phase stream.

31. The system of claim 27, further comprising a pump configured to pump the liquid phase stream from the phase separator through the liquid flow meter.

32. The system of claim 27, further comprising a second volumetric receptacle adapted to receive the liquid phase stream.

33. The system of claim 27, further comprising a density meter configured to assess a density of at least a portion of the liquid phase stream.

34. The system of claim 27, further comprising a second gas chromatograph arranged to receive at least a portion of the liquid phase stream.

35. The system of claim 27, wherein the controller is configured to control a flow of the reservoir fluid, the vapor phase stream, the liquid phase stream, or a combination thereof.

36. The system of claim 27, wherein the controller is configured to initiate flow of the reservoir fluid sample to the volumetric receptacle.

37. The system of claim 27, wherein the controller is configured to initiate flow of the reservoir fluid sample to the volumetric receptacle at a pre-selected time, interval, or combination thereof.

38. The system of claim 27, wherein the controller is configured to control a flow rate of the reservoir fluid from the volumetric receptacle to the phase separator.

39. The system of claim 27, wherein the controller is configured to select a source of the reservoir fluid sample.

40. The system of claim 27, wherein the liquid flow meter is configured to detect an interface between an oil component of the liquid phase stream and a gas.

* * * * *